United States Patent
Perry et al.

[11] Patent Number: 6,077,923
[45] Date of Patent: Jun. 20, 2000

[54] FRAGRANCE RELEASING NON-VOLATILE POLYMERIC SILOXANES

[75] Inventors: Robert J. Perry, Niskayuna; John Alfred Kilgour, Clifton Park, both of N.Y.

[73] Assignee: General Electric Company, Pittsfield, Mass.

[21] Appl. No.: 09/421,493

[22] Filed: Oct. 20, 1999

Related U.S. Application Data

[62] Division of application No. 09/143,498, Aug. 28, 1998.

[51] Int. Cl.⁷ .................................................. L08G 77/06
[52] U.S. Cl. ............................... 528/26; 528/15; 424/401
[58] Field of Search .............................. 424/401; 528/15, 528/26

[56] References Cited

U.S. PATENT DOCUMENTS

| | | |
|---|---|---|
| 2,679,496 | 5/1954 | Bunnell . |
| 3,271,305 | 9/1966 | Allen et al. . |
| 3,779,987 | 12/1973 | Razzano . |
| 4,445,641 | 5/1984 | Baker et al. . |
| 4,500,725 | 2/1985 | Yemoto et al. . |
| 4,524,018 | 6/1985 | Yemoto et al. . |
| 4,908,208 | 3/1990 | Lee et al. . |
| 5,008,115 | 4/1991 | Lee et al. . |
| 5,071,704 | 12/1991 | Fischel-Ghodsian . |
| 5,130,171 | 7/1992 | Prud'Homme et al. . |
| 5,160,494 | 11/1992 | Krzysik et al. . |
| 5,176,903 | 1/1993 | Goldberg et al. . |
| 5,185,155 | 2/1993 | Behan et al. . |
| 5,234,689 | 8/1993 | Lindauer et al. . |
| 5,324,444 | 6/1994 | Berry et al. . |
| 5,372,806 | 12/1994 | Holloway . |
| 5,387,411 | 2/1995 | Abrutyn et al. . |
| 5,387,622 | 2/1995 | Yamamoto . |
| 5,449,512 | 9/1995 | Simmons . |
| 5,490,982 | 2/1996 | Siciliano . |
| 5,500,223 | 3/1996 | Behan et al. . |
| 5,508,259 | 4/1996 | Holzner et al. . |
| 5,525,555 | 6/1996 | Zank . |
| 5,525,588 | 6/1996 | Michetti . |

FOREIGN PATENT DOCUMENTS

| | | |
|---|---|---|
| 1 073 325 | 6/1967 | United Kingdom . |
| 2041964 | 9/1980 | United Kingdom . |
| WO 9628497 | 9/1996 | WIPO . |

*Primary Examiner*—Robert Dawson
*Assistant Examiner*—Jeffrey B. Robertson
*Attorney, Agent, or Firm*—Michelle Bugbee; Kenneth S. Wheelock

[57] ABSTRACT

A fragrance releasing siloxane comprising a substituent having the formula $(R^1O)_a(R^2O)_b(R^3O)_c(R^4)_d(R^5)_eSiR^U$ with $R^U$ a two to forty atom divalent hydrocarbon radical where $R^1$, $R^2$ and $R^3$ are derived from the group of fragrant esters, ketones, or aldehydes, each independently having the structure: $R^7$—CH=C(O—)—$R^8$, with $R^4$ and $R^5$ selected from the group consisting of monovalent hydrocarbon radical having from one to forty carbon atoms and monovalent alkoxy radicals having from one to forty carbon atoms, where the subscript a has a value ranging from 1 to 3 and the subscripts b, c, d, and e have values ranging from 0 to 2 subject to the limitation that $a+b+c+d+e=3$; $R^7$ is selected from the group consisting of hydrogen and monovalent hydrocarbon radicals having from one to one hundred carbon atoms and $R^8$ is selected from the group consisting of hydrogen and monovalent hydrocarbon radicals having from one to one hundred carbon atoms where the subscript a has a value ranging from 1 to 3 and the subscripts b, c, d, and e have values ranging from 0 to 2 subject to the limitation that $a+b+c+d+e=3$.

10 Claims, No Drawings

FRAGRANCE RELEASING NON-VOLATILE POLYMERIC SILOXANES

This is a divisional of co-pending application Ser. No. 09/143,498 filed on Aug. 28, 1998.

FIELD OF THE INVENTION

The present invention relates to non-volatile oligomeric or polymeric siloxanes which may be linear, branched or cross-linked, suitable for use in a variety of applications including personal care formulations, house-hold products, automotive, textiles and molding materials wherein the non-volatile polymeric siloxane has been chemically modified to release a fragrant molecule upon hydrolysis. The present invention further relates to such molecules where the rate of fragrant molecule release is sufficiently slow so that products formulated with the modified polymeric non-volatile siloxane exhibit a desirable fragrance for long periods of time.

BACKGROUND OF THE INVENTION

The slow sustained release of a fragrant molecule is a highly desirable trait in many personal care products. A number of means have been proposed and implemented to achieve this goal. Among these means are dissolving or suspending fragrant compounds in personal care emulsions (U.S. Pat. Nos. 5,525,588; 5,525,555; 5,490,982; and 5,372,806), encapsulation of a fragrant compound (U.S. Pat. Nos. 5,500,223; 5,324,444; 5,185,155; 5,176,903; and 5,130,171), dissolving a fragrant compound into a hydrophobic phase such as a silicone (U.S. Pat. Nos. 5,449,512; 5,160,494 and 5,234,689), incorporation of a fragrant compound into cross-linked polymers (U.S. Pat. Nos. 5,387,622 and 5,387,411), incorporation of fragrant compounds into permeable laminates (U.S. Pat. Nos. 5,071,704 and 5,008,115), incorporation of fragrant compounds into matrices that soften at body temperature (U.S. Pat. No. 4,908,208), incorporation of fragrant compounds into rate controlling membranes (U.S. Pat. No. 4,445,641) and derivatization of silanes with fragrant alcohols to form alkoxy silanes (U.S. Pat. Nos. 4,524,018 and 4,500,725). All of these approaches suffer from one or more of the following problems: 1) the material is not stable in a personal care formulation, 2) the material is not easy or convenient to prepare, or 3) the material does not release the fragrant compound in a slow and sustained fashion.

SUMMARY OF THE INVENTION

The present invention provides for a fragrance releasing siloxane having the formula:

$$M_f M^F{}_g D_h D^F{}_i T_j T^F{}_k Q_l$$

where M has the formula $R^7R^8R^9SiO_{1/2}$; $M^F$ has the formula $R^7R^8R^FSiO_{1/2}$; D has the formula $R^{10}R^{11}SiO_{2/2}$; $D^F$ has the formula $R^{10}R^FSiO_{2/2}$; T has the formula $R^{12}SiO_{3/2}$; $T^F$ has the formula $R^FSiO_{3/2}$; and Q has the formula $SiO_{4/2}$ where $R^7$, $R^8$, $R^9$, $R^{10}$, $R^{11}$ and $R^{12}$ are each independently selected for each M, $M^F$, D, $D^F$, T and $T^F$ from the group of one to forty carbon atom monovalent alkyl or alkoxy radicals and one to forty carbon atom monovalent aryl or aryloxy radicals where the subscripts f or g are positive, and one or more of the subscripts h, i, j, k or l are positive, subject to the limitation that one of the subscripts g, i, or k is one or greater than one; where $R^F$ has the formula $(R^1)_a(R^2)_b(R^3)_c(R^4)_d(R^5)_eSiR^U$ with $R^U$ a two to forty atom divalent hydrocarbon radical, where $R^1$, $R^2$ and $R^3$ are derived from the group of fragrant esters, ketones, or aldehydes, each independently having the structure:

$$R^7\text{---}CH\!=\!C(O\text{---})\text{---}R^8,$$

with $R^4$ and $R^5$ selected from the group consisting of monovalent hydrocarbon radical having from one to forty carbon atoms and monovalent alkoxy radicals having from one to forty carbon atoms, where the subscript a has a value ranging from 1 to 3 and the subscripts b, c, d, and e have values ranging from 0 to 2 subject to the limitation that a+b+c+d+e=3; $R^7$ is selected from the group consisting of hydrogen and monovalent hydrocarbon radicals having from one to one hundred carbon atoms and $R^8$ is selected from the group consisting of hydrogen and monovalent hydrocarbon radicals having from one to one hundred carbon atoms where the subscript a has a value ranging from 1 to 3 and the subscripts b, c, d, and e have values ranging from 0 to 2 subject to the limitation that a+b+c+d+e=3. The present invention also provides for compositions that comprise a fragrance releasing siloxane. Of particular use are cosmetic compositions that comprise a fragrance releasing siloxane

DETAILED DESCRIPTION OF THE INVENTION

The compounds of the present invention introduce fragrant moieties via hydrosilylation of an olefinic silane molecule. These siloxane molecules are useful in a variety of personal care compositions. The present invention is directed to new compositions of matter that are siloxanes that release a fragrant aldehyde, ketone or ester upon hydrolysis.

The olefinic silanes utilized by the present invention are described by the formula:

$$(R^1)_a(R^2)_b(R^3)_c(R^4)_d(R^5)_eSiR^6$$

where $R^1$, $R^2$ and $R^3$ are derived from the group of fragrant esters, ketones, or aldehydes, each independently having the structure:

$$R^7\text{---}CH_2(C\!=\!O)\text{---}R^8$$

wherein the fragrant ester, ketone or aldehyde is capable of exhibiting the enol form of the carbonyl moiety under reaction conditions as shown:

$$R^7\text{---}CH_2(C\!=\!O)\text{---}R^8 \rightarrow R^7\text{---}CH\!=\!C(OH)\text{---}R^8$$

and which will react through the enol hydroxyl group to form a carbon-oxygen-silicon linkage (i.e. $R^7$—CH=C(O—)—$R^8$ where the hyphen after the oxygen in the formula indicates the species is a monovalent radical and independently describes $R^1$, $R^2$ and $R^3$), with $R^4$ and $R^5$ selected from the group consisting of monovalent hydrocarbon radical having from one to forty carbon atoms and monovalent alkoxy radicals having from one to forty carbon atoms, $R^6$ a two to forty atom monovalent unsaturated hydrocarbon radical containing a terminal olefinic or acetylenic moiety where the subscript a has a value ranging from 1 to 3 and the subscripts b, c, d, and e have values ranging from 0 to 2 subject to the limitation that a+b+c+d+e=3; $R^7$ is selected from the group consisting of hydrogen and monovalent hydrocarbon radicals having from one to one hundred carbon atoms and $R^8$ is selected from the group consisting of hydrogen and monovalent hydrocarbon radicals having from one to one hundred carbon atoms. It should be noted that the structure:

$$R^7—CH=C(O—)—R^8$$

is a conjugate structure that corresponds to the enolate structure:

$$R^7—CH=C(OH)—R^8$$

but missing the hydroxyl hydrogen. In the structure:

$$R^7—CH=C(O—)—R^8$$

the hyphen after the oxygen atom indicates a univalent bonding site wherein the structure is a monovalent radical. As used herein the phrase from one to one hundred carbon atoms is chosen wherein the class of available fragrant esters, ketones, and aldehydes is subtended by the formula $R^7—CH_2(C=O)—R^8$. As used herein, the phrase monovalent hydrocarbon radical includes both aliphatic and aromatic monovalent hydrocarbon radicals that may also include hetero-atoms such as oxygen, nitrogen, sulfur and the halogens, fluorine, chlorine, bromine and iodine.

The fragrant carbonyl containing species are selected from the group consisting of 3-methyl-3-(3-(1-methylethylphenyl))propanal, 2-methyl-3-(4-t-butylphenyl)propanal, 3-phenylpropional, 2-phenylpropional, propional, isobutyral, 2-methylbutyral, hexanal, octanal, nonanal, decanal, 3,7-dimethyl-1-al, p-tolylacetaldehyde, phenylacetaldehyde, 4-(3)(4-methyl-3-pentenyl)-3-cyclohexen-carbaldehyde, 2,6-dimethyl-5-heptenal, 3,7-dimethyl-2,6-octadienal, trans-4-decenal, cyclamen aldehyde, 4-(p-methoxyphenyl)-2-butanone, acetophenone, 2-pentanone, 2-butanone, 2-heptanone, 3-heptanone, 2-decanone, 3-penten-2-one, 6-methyl-5-hepten-2-one, geranylacetone, ionone, 5-methyl-alpha-ionone, 2-acetonaphtone, 2-methyl-3-phenylpropan-2-yl acetate, linalyl acetate, menthanyl acetate, 2-phenylethyl acetate, tetrahydrolinalyl acetate, phenethyl propionate, phenethylhexanoate, and butyl acetate.

The following synthetic examples are intended to illustrate the general synthetic reactions schemes that a person having ordinary skill in the art of silicones chemistry would typically employ in order to prepare the olefinic silanes used by the present invention. These reaction schemes are thus illustrative only and do not represent the only synthetic pathways that may be utilized. An example of the reaction scheme using a fragrant carbonyl containing moiety, 2-methyl-3-(4-t-butylphenyl)propanal:

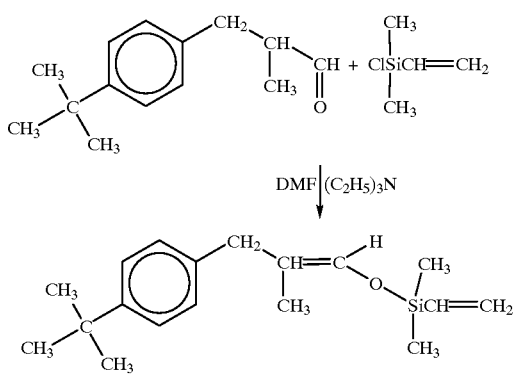

Note that DMF is dimethylformamide. This reaction scheme may also be used to prepare the 3-methyl-3-(3-(1-methylethylphenyl))propanal derivative:

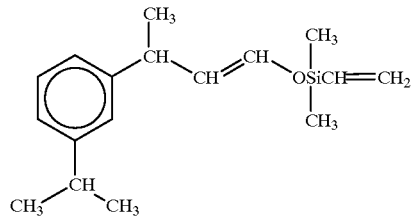

The reaction of fragrant carbonyl containing species, i.e. esters, ketones and aldehydes, requires the establishment of the keto enol tautomeric equilibrium.

Tautomerism is the chemical phenomenon of the establishment of an equilibrium between two or more structurally distinct compounds. In nearly all cases, the difference between one tautomeric form of the equilibrium compounds and the other is the isomeric placement of a hydrogen atom. A prevalent form of tautomerism is the tautomeric equilibrium established between a carbonyl compound (i.e. one containing a carbonyl group) and having a hydrogen atom alpha to the carbonyl group, i.e. an α hydrogen:

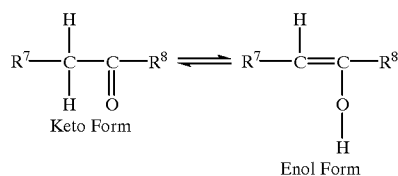

Generally the equilibrium constant favors the keto form and the equilibrium lies well to the left. The extent of enolization is greatly affected by solvent, concentration and temperature. When a strong base is present, both the enol and the keto form can lose a hydrogen ion (a proton), forming an enolate anion:

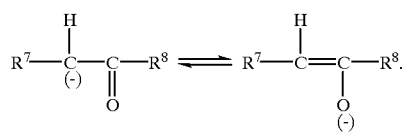

Since both of these structures differ only in the placement of electrons, these are canonical forms of the same ion rather than tautomeric isomers. Because oxygen is more electronegative than carbon, the predominate canonical form is the one where the ionic charge is more localized on the oxygen atom. While the tautomeric equilibrium between enols and ketones or aldehydes is not normally a preparative reaction, the equilibrium must occur since ketones and aldehydes often react through their enol forms as they do instantly in the preparation of the compounds of the present invention. For a more detailed explanation of this chemistry see J. March "Advanced Organic Chemistry," John Wiley & Sons, New York (1985), pp. 66–68 and 527–529 and references therein.

The fragrance releasing siloxanes of the present invention are prepared from an organohydrogen siloxane via conventional hydrosilylation using the fragrance bearing olefinic silane as the alkenyl source, an example of this reaction being:

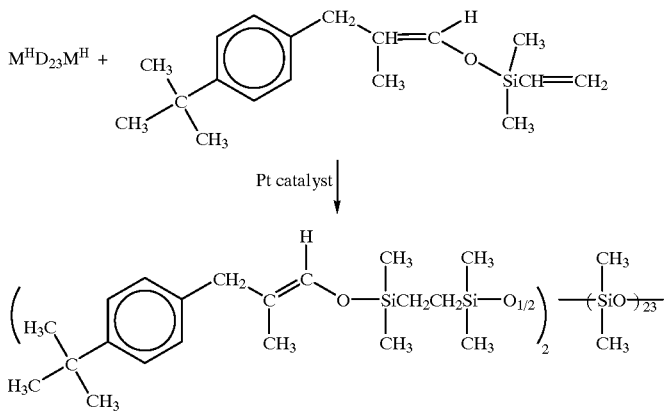

In this specific instance, $M^H$ has the formula $R^7R^8HSiO_{1/2}$ and D has the formula $R^{10}R^{11}SiO_{2/2}$ where $R^7$, $R^8$, $R^{10}$, and $R^{11}$ are all methyl groups.

Thus an organohydrogensiloxane having the formula:

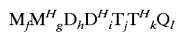

where M has the formula $R^7R^8R^9SiO_{1/2}$; $M^H$ has the formula $R^7R^8HSiO_{1/2}$; D has the formula $R^{10}R^{11}SiO_{2/2}$; $D^H$ has the formula $R^{10}HSiO_{2/2}$; T has the formula $R^{12}SiO_{3/2}$; $T^H$ has the formula $HSiO_{3/2}$; and Q has the formula $SiO_{4/2}$ where $R^7$, $R^8$, $R^9$, $R^{10}$, $R^{11}$ and $R^{12}$ are each independently selected for each M, $M^H$, D, $D^H$, and T from the group of one to forty carbon atom monovalent alkyl or alkoxy radicals and one to forty carbon atom monovalent aryl or aryloxy radicals where the subscripts f or g are positive, and one or more of the subscripts h, i, j, k or l are positive, subject to the limitation that one of the subscripts g, i, or k is one or greater than one.

The organohydrogensiloxane is reacted under hydrosilylation conditions to produce a fragrance releasing siloxane having the formula:

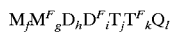

where the components and subscripts satisfy the previous definitions and requirements and $M^F$ has the formula $R^7R^8R^FSiO_{1/2}$; $D^F$ has the formula $R^{10}R^FSiO_{2/2}$; and $T^F$ has the formula $R^FSiO_{3/2}$; where $R^F$ has the formula $(R^1)_a(R^2)_b(R^3)_c(R^4)_d(R^5)_eSiR^U$ with $R^U$ a two to forty atom divalent hydrocarbon radical where the subscripts and components are as previously defined. This non-volatile silicone undergoes a slow hydrolysis under most conditions of use whereby the silicone releases a fragrant alcohol upon hydrolysis. This imparts a desirable odor to many different useful compositions such as cosmetics and household products.

The hydrosilylation reaction is conventionally carried out in the presence of a hydrosilylation catalyst selected from the group of ruthenium, osmium, rhodium, iridium, palladium and platinum hydrosilylation catalysts. Exemplary of such catalysts are those described in U.S. Pat. Nos. 2,823,218; 3,159,601; 3,159,662; and 3,775,452.

The compositions of the present invention further provide that the fragrance releasing silicone have one or more substituents $R^1$, $R^2$, or $R^3$ where each substituent is independently selected whereby a fragrant aldehyde, ketone or ester resulting from hydrolysis of said silicone is selected from the group of fragrant esters, ketones, or aldehydes consisting of 3-methyl-3-(3-(1-methylethylphenyl))propanal, 2-methyl-3-(4-t-butylphenyl)propanal, 3-phenylpropional, 2-phenylpropional, propional, isobutyral, 2-methylbutyral, hexanal, octanal, nonanal, decanal, 3,7-dimethyl-1-al, p-tolylacetaldehyde, phenylacetaldehyde, 4-(3)(4-methyl-3-pentenyl)-3-cyclohexen-carbaldehyde, 2,6-dimethyl-5-heptenal, 3,7-dimethyl-2,6-octadienal, trans-4-decenal, cyclamen aldehyde, 4-(p-methoxyphenyl)-2-butanone, acetophenone, 2-pentanone, 2-butanone, 2-heptanone, 3-heptanone, 2-decanone, 3-penten-2-one, 6-methyl-5-hepten-2-one, geranylacetone, ionone, 5-methyl-alphaionone, 2-acetonaphtone, 2-methyl-3-phenylpropan-2-yl acetate, linalyl acetate, menthanyl acetate, 2-phenylethyl acetate, tetrahydrolinalyl acetate, phenethyl propionate, phenethylhexanoate, and butyl acetate.

The fragrance releasing compounds of the present invention are particularly suited to incorporation into personal care products to impart a desirable long lasting fragrance to the products. Suitable uses include but are not limited to deodorants, antiperspirants, skin creams, facial creams, hair care products such as shampoos, mousses, styling gels, protective creams, shaving creams, after shave, cologne, perfume, color cosmetics such as lipsticks, foundations, blushes, makeup, and mascara; and other cosmetic formulations where other silicon containing components have been added and where it is desirable to impart a fragrance. Incorporation of small amounts of the compositions of the present invention into fragrance products such as shaving lotions, colognes, toilet water, and perfumes can impart a desirable long lasting fragrance to these products. Further, the siloxanes of the present invention may incorporated into other products where it is desirable to mask unpleasant odors with a pleasant fragrance for example household cleaning products such as waxes and polishes, automobile cleaning products such as waxes and polishes, detergents, textile coatings, paints, varnishes and the like subject to the limitation that the silane of the present invention be compatible or capable of being rendered compatible with the product in which it is incorporated.

Experimental

Vinylsilane 3 was prepared by in-situ formation of the enolate of 1, followed by displacement of the chloro group from 2.

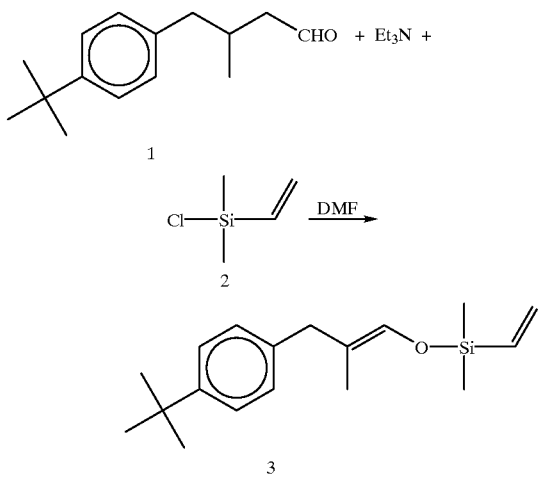

Hydrosilation of 3 onto a hydride terminated polysiloxane gave polymer 4.

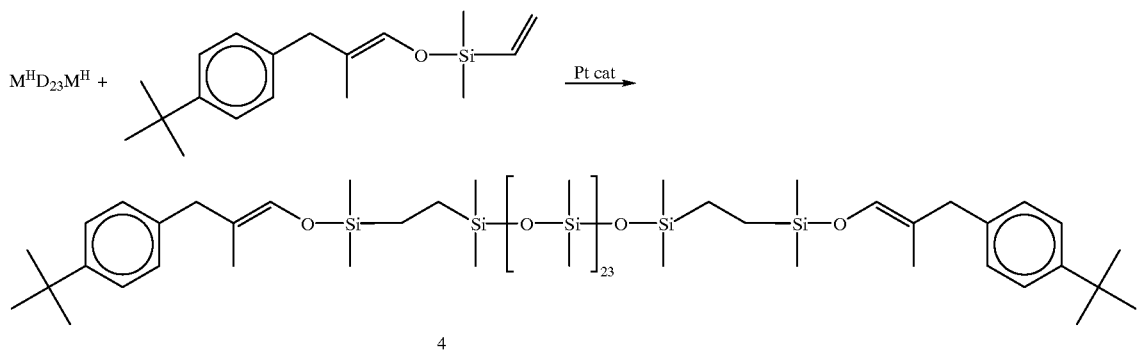

Hydrolysis Reactions

Polymer 4 was subjected to hydrolysis in aqueous base and acid under basic conditions (NaOH), release of the 2-methyl-3-(4-t-butylphenyl)propanal fragrance moiety was complete within one hour as shown in Table 1. Under strong acid conditions (trifluoroacetic acid), approximately one hour was required for lease. Under less harsh conditions using acetic acid, release was completed in about 7 hours. These examples demonstrate that fragrance moieties can be effectively released over time.

TABLE 1

Release of 2-methyl-3-(4-t-butylphenyl)propanal from Polymer 4.

| Time (h) | CH3COOH | CF3COOH | NaOH |
| --- | --- | --- | --- |
| 0 | 15.7 | 18.7 | |
| .61 | 24.3 | | |
| 3.58 | 65.2 | | |
| 4.4 | 61.7 | | |
| 7.3 | 72.4 | | |
| 0.5 | | 35.3 | |
| .85 | | 42.5 | |
| 1.17 | | 44.7 | |
| 1.5 | | 44.7 | |
| 4.13 | | 38.6 | |
| 0.1 | | | 66.4 |

TABLE 1-continued

Release of 2-methyl-3-(4-t-butylphenyl)propanal from Polymer 4.

| Time (h) | CH3COOH | CF3COOH | NaOH |
| --- | --- | --- | --- |
| 0.43 | | | 79.3 |
| 2.5 | | | 82.1 |

Dimethylvinylsilane 3—A 100 mL 3-neck round bottom flask equipped with a stir-bar, a thermometer, a condenser and a nitrogen inlet was charged with dimethylvinylchlorosilane (4.1 mL, 0.030 moles), 2-methyl-3-(4-t-butylphenyl)propanal (5.0 g, 0.024 moles), triethylamine and N,N-dimethylformamide (DMF, 20 mL) and heated to 80° C. for 22 h. the mixture was diluted with 100 mL of Isopar-C®, and the mixture was washed three times with cold saturated aqueous sodium bicarbonate, then cold 1N HCl, then bicarbonate, then dried over $MgSO_4$ and stripped to give 6.4 g (90%) product.

Preparation of Polymer 4—Vinyl silane 3 (5.0 g, 0.017 mole) and a divinyltetramethyldisiloxane platinum complex (2 mL of 5% solution in isopropanol) were heated to 65° C. and then $M^H D_{23} M^H$ (16.0 g, 0.0086 mole) was added slowly over 0.5 h. The reaction was allowed to continue for 5.5 h then cooled to give polymer 4.

Hydrolysis of Polymer 4 with NaOH—The polymer (108.1 mg, 0.045 mmol) and dodecane (internal standard, 18.6 mg, 0.1092 mmol) was dissolved in THF (2.0 g) and then treated with 0.35 wt % aqueous NaOH solution (0.31 g). Aliquots were removed at timed intervals for GC analysis. Table 1 shows the data for the release profile of 2-methyl-3-(4-t-butylphenyl)propanal from the polymer.

Hydrolysis of Polymer 4 with $CF_3COOH$—The polymer, polymer 4, (102.5 mg, 0.0427 mmol) and dodecane (internal standard, 20.9 mg, 0.1227 mmol) was dissolved in THF (2.0 g) and then treated with 1.0 wt % aqueous $CF_3COOH$ solution (0.30 g). Aliquots were removed at timed intervals for GC analysis. Table 1 shows the data for the release profile of 2-methyl-3-(4-t-butylphenyl)propanal from the polymer.

Hydrolysis of Polymer 4 with $CH_3COOH$—The polymer, polymer 4, (111.1 mg, 0.0463 mmol) and dodecane (internal standard, 18.8 mg, 0.110 mmol) was dissolved in THF (2.0 g) and then treated with 0.54 wt % aqueous $CH_3COOH$ solution (0.32 g). Aliquots were removed at timed intervals for GC analysis. Table 1 shows the data for the release profile of 2-methyl-3-(4-t-butylphenyl)propanal from the polymer.

What is claimed is:
1. A composition comprising a fragrance releasing siloxane having the formula:

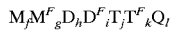

where M has the formula $R^7R^8R^9SiO_{1/2}$; $M^F$ has the formula $R^7R^8R^FSiO_{1/2}$; D has the formula $R^{10}R^{11}SiO_{2/2}$; $D^F$ has the formula $R^{10}R^FSiO_{2/2}$; T has the formula $R^{12}SiO_{3/2}$; $T^F$ has the formula $R^FSiO_{3/2}$; and Q has the formula $SiO_{4/2}$ where $R^7, R^8, R^9, R^{10}, R^{11}$ and $R^{12}$ are each independently selected for each M, $M^F$, D, $D^F$, T and $T^F$ from the group of one to forty carbon atom monovalent alkyl or alkoxy radicals and six to forty carbon atom monovalent aryl or aryloxy radicals where the subscripts f or g are positive, and one or more of the subscripts h, i, j, k or l are positive, subject to the limitation that one of the subscripts g, i, or k is one or greater than one; where $R^F$ has the formula $(R^1)_a(R^2)_b(R^3)_c(R^4)_d(R^5)_eSiR^U$ with $R^U$ a two to forty atom divalent hydrocarbon radical, where $R^1$, $R^2$ and $R^3$ are derived from the group of fragrant esters, ketones, or aldehydes, each independently having the structure:

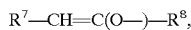

with $R^4$ and $R^5$ selected from the group consisting of monovalent hydrocarbon radical having from one to forty carbon atoms and monovalent alkoxy radicals having from one to forty carbon atoms, where the subscript a has a value ranging from 1 to 3 and the subscripts b, c, d, and e have values ranging from 0 to 2 subject to the limitation that a+b+c+d+e=3; $R^7$ is selected from the group consisting of hydrogen and monovalent hydrocarbon radicals having from one to one hundred carbon atoms and $R^8$ is selected from the group consisting of hydrogen and monovalent hydrocarbon radicals having from one to one hundred carbon atoms where the subscript a has a value ranging from 1 to 3 and the subscripts b, c, d, and e have values ranging from 0 to 2 subject to the limitation that a+b+c+d+e=3.

2. The fragrance releasing siloxane of claim 1 wherein the subscript a has a value of 2.

3. The fragrance releasing siloxane of claim 1 wherein the subscript a has a value of 3.

4. The fragrance releasing siloxane of claim 1 where the subscript l is 0.

5. The fragrance releasing siloxane of claim 4 where the subscript k is 0.

6. The fragrance releasing siloxane of claim 5 where the subscript j is 0.

7. The fragrance releasing siloxane of claim 6 where the subscript i is 0.

8. The fragrance releasing siloxane of claim 7 where the subscript j is 0.

9. The fragrance releasing siloxane of claim 7 where $R^1$, $R^2$ and $R^3$ are derived from the group of fragrant esters, ketones, or aldehydes consisting of 3-methyl-3-(3-(1-methylethylphenyl))propanal, 2-methyl-3-(4-t-butylphenyl) propanal, 3-phenylpropional, 2-phenylpropional, propional, isobutyral, 2-methylbutyral, hexanal, octanal, nonanal, decanal, 3,7-dimethyl-1-al, p-tolylacetaldehyde, phenylacetaldehyde, 4-(3)(4-methyl-3-pentenyl)-3-cyclohexen-carbaldehyde, 2,6-dimethyl-5-heptenal, 3,7-dimethyl-2,6-octadienal, trans-4-decenal, cyclamen aldehyde, 4-(p-methoxyphenyl)-2-butanone, acetophenone, 2-pentanone, 2-butanone, 2-heptanone, 3-heptanone, 2-decanone, 3-penten-2-one, 6-methyl-5-hepten-2-one, geranylacetone, ionone, 5-methyl-alpha-ionone, 2-acetonaphtone, 2-methyl-3-phenylpropan-2-yl acetate, linalyl acetate, menthanyl acetate, 2-phenylethyl acetate, tetrahydrolinalyl acetate, phenethyl propionate, phenethylhexanoate, and butyl acetate.

10. A cosmetic composition selected from the group consisting of deodorants, antiperspirants, skin creams, facial creams, hair care products shampoos, mousses, styling gels, protective creams, shaving creams, after shave, cologne, perfume, lipsticks, foundations, blushes, makeup, and mascara; and other cosmetic formulations where other silicon containing components have been added comprising the fragrance releasing siloxane of claim 1.

\* \* \* \* \*